United States Patent [19]
Savord

[11] Patent Number: 5,431,167
[45] Date of Patent: Jul. 11, 1995

[54] METHOD AND APPARATUS FOR INCREASING THE FRAME RATE AND RESOLUTION OF A PHASED-ARRAY IMAGING SYSTEM

[75] Inventor: Bernard J. Savord, Andover, Mass.

[73] Assignee: Hewlett-Packard Company, Palo Alto, Calif.

[21] Appl. No.: 184,419

[22] Filed: Jan. 21, 1994

Related U.S. Application Data

[62] Division of Ser. No. 870,388, Apr. 17, 1992, Pat. No. 5,318,033.

[51] Int. Cl.$^6$ ................................................ A61B 8/00
[52] U.S. Cl. ................................................ 128/660.07
[58] Field of Search .................. 128/660.07, 661.01; 73/625–626; 367/11

[56] References Cited

U.S. PATENT DOCUMENTS 5,197,037  3/1993  Leavitt .................. 128/661.01 X Primary Examiner—F. Jaworski

[57] ABSTRACT

Scan conversion or data interpolation is performed on the signal generated by acoustic transducers in an acoustic imaging system before the signal is processed by detecting and limiting it. This processing uses signal phase information, which is normally lost during the image reconstruction process, to increase image resolution. A nonlinear interpolation scheme is used during the scan conversion process used to convert the data generated by acoustic transducers into data suitable for visual display in order to more accurately generate interpolated data points. A nonlinear angular spacing between acoustic lines is used to increase the image frame rate can be increased without decreasing image resolution. The frame rate of the acoustic imaging system can also be increased by interpolating the signals generated by the transducers before they are provided to beamforming circuits.

14 Claims, 12 Drawing Sheets

METHOD AND APPARATUS FOR INCREASING THE FRAME RATE AND RESOLUTION OF A PHASED-ARRAY IMAGING SYSTEM

This is a divisional of copending application Ser. No. 07/870,388 filed on Apr. 17, 1992 and now U.S. Pat. No. 5318033

FIELD OF THE INVENTION

This invention relates to phased-array acoustic systems and, in particular, to ultrasonic phased-array imaging systems.

BACKGROUND OF THE INVENTION

Ultrasonic imaging systems for producing real-time images of internal portions of the human body are well-known. In one such system, an array of ultrasonic transducers placed in contact with the body converts short electrical pulses into corresponding pressure waves. The electrical pulses can be applied to each individual transducer in the array and by choosing the application time of the pulses to each transducer relative to the other transducers in the array, the pressure waves generated by each transducer can be formed into a "transmit beam" which propagates in a predetermined direction from the array.

As the pressure waves in the transmit beam pass through the body, a portion of the acoustic energy is reflected back towards the transducer array whenever the waves encounter tissues having different acoustic characteristics. An array of receiving transducers (which may be the same as the transmitting array) is provided for converting the reflected pressure pulses into corresponding electrical pulses. The reflected pressure pulses are received by each transducer in the receiving array and by suitably choosing relative delays between the signals generated by each transducer and combining the signals, the received pressure waves located in a "receiving beam" can be emphasized preferentially to other pressure pulses. As with the transmit beam, the relative transducer delays can be adjusted so that the receiving beam extends in any desired direction from the transducer array.

It is also possible to "focus" the received acoustic signals at a point along the receiving beam. This is done by selectively adjusting relative signal delays between the transducers so that the electrical signals generated by the receiving transducers are superimposed in time for signals received from a point along the receiving beam at a predetermined distance from the transducer array, but are not superimposed for other signals. Consequently, when the signals are combined, a strong signal is produced from signals corresponding to this point whereas signals arriving from other points at different times have random phase relationships and therefore destructively interfere.

A two-dimensional image plot or sector image can be generated with this system by adjusting the acoustic transducers to generate or "shoot" a transmit beam at a selected angular direction from the transducer array. The receiving transducers are then adjusted to generate a receiving beam at the same angle as the transmitting beam. The receiving transducers are adjusted to focus the receiving beam at sequentially increasing distances from the transducer array along the predetermined transmit beam angle. The received signals for each sequential focal point are stored. The transmit and receive beams are then moved by a predetermined angular amount and the process of acquiring signals is repeated. The started signals are then processed to generate a wedge-shaped acoustic image called a sector.

Since the distances between any desired focal point along the receiving beam and the various receiving transducers are different, the reflected pressure pulses arrive at the transducers at different times, thereby generating electrical signals at different times. It is therefore necessary to introduce compensating electrical delays between each transducer and the signal summing point so that the time of arrival of all of the electrical signals at the summing point is the same regardless of which transducer is involved. The collection of transducer compensating delays and the signal summing circuitry is normally referred to as a "beamformer" and is described, for example, in U.S. Pat. No. 4,140,022 issued to the assignee of the present invention. The description of the beamformer apparatus described therein is hereby incorporated by reference.

The output of the beamformer is generally a radio-frequency signal representing the amplitude of the received pressure pulses. The signals are often a function of the angle ($\Theta$) of the receive beam and the radial distance (R) along the receive beam at which the focal point occurs. Consequently, the signals are said to be in R-$\Theta$ coordinates. It is also possible, using conventional construction methods, to construct a beamformer which generates scanning information in other coordinate systems, such as a linear scan. However, by considering small, localized areas, signals expressed in these other coordinate systems can be converted to R-$\Theta$ coordinates. Therefore, the following discussion will assume R-$\Theta$ coordinates without loss of generality.

Generally, the signals are displayed on a display monitor such as a television or raster-scan monitor and, thus, the format of the signals must be converted from R-$\Theta$ coordinates to the X-Y coordinates used in the television display. This conversion is performed by a device called an X-Y scan converter. Since actual data is available in R-$\Theta$ coordinates at discrete angular positions, the scan converter must generate the required X-Y values by interpolating between the R-$\Theta$ coordinate values. The construction and operation of such scan converters is well-Known. For example, scan converters are discussed in detail in U.S. Pat. Nos. 4,468,747 and 4,471,449, both assigned to the assignee of the present invention. The description of these patents is hereby incorporated by reference and, accordingly, the detailed construction of scan converters will not be discussed further herein.

It has been found that with some conventional scan converter systems certain problems occur. One such problem is that the images produced by the system often have "artifacts" in the reconstructed image. Artifacts are visual anomalies that appear in the displayed image but are not present on the actual object. Such anomalies may consist of radiating lines, checkerboard patterns or speckles and are generally related to imperfect reconstruction of the image.

Another problem with prior art systems is that they often have limited resolution. One known method of increasing image resolution is to increase the number of acoustic lines which are shot by reducing the angular increment between lines. Obviously, such an approach increases the overall time necessary to obtain the acoustic data and reconstruct the image. Since many ultrasonic imaging systems are used for imaging moving objects such as heart valves, it is of prime importance to generate an image as fast as possible (by increasing the "frame rate" or the number of images generated per unit time) so that the object motion can be depicted as accurately as possible. The frame rate can be increased by decreasing the number of lines which are shot to produce each image. However, as previously discussed, this also reduces the overall resolution of the image. Consequently, in prior art systems there has been a trade-off between resolution and frame rate.

Accordingly, it is an object of the present invention to provide a method and apparatus for increasing resolution without correspondingly reducing the frame rate of the system.

It is a further object of the present invention to increase the signal-to-noise ratio of the system or increase the frame rate without correspondingly increasing the amount of circuitry or time involved generating an acoustic image.

It is a further object of the present invention to utilize additional information normally discarded during the prior art reconstruction process to provide better resolution upon reconstruction.

It is a further object of the present invention to reduce artifacts in the acoustic image produced by imperfect prior art reconstruction processes.

It is still a further object of the present invention to increase the resolution without increasing the acoustic line density.

SUMMARY OF THE INVENTION

The foregoing objects are achieved and the foregoing problems are solved in one illustrative embodiment of the invention in which an acoustic imaging system is treated as a Nyquist sampled data system. In accordance with one aspect of the invention, the signal processing order is changed in order to use signal phase information, which is normally lost during the reconstruction process, to increase image resolution. In particular, in the inventive system and method, scan conversion or data interpolation is performed on the signal generated by the transducers before the signal is processed by detecting and limiting it.

In accordance with another aspect of the invention, a nonlinear interpolation scheme is used during the scan conversion process to convert the R-$\Theta$ data into X-Y data. It has been found that prior art linear interpolation underestimates the image intensity between data and that a nonlinear interpolation reduces the underestimation. More particularly, in accordance with the invention, the image data value between two lines is estimated by using an interpolator which estimates the data in accordance with numerical values which describe the main lobe of a sine (sin x/x) function.

In an additional embodiment of the invention, it has been found that, for imaging systems which use linear transducer arrays, when the transmit and receive beams are directed to a position which forms a large angle relative to a line perpendicular to the array, the effective phased array aperture is reduced by the cosine of the beam or steering angle. This reduction results in a wider beam width. Accordingly, a larger angular spacing between acoustic lines can be used to obtain the same image resolution as an image obtained with equal line spacing between acoustic lines. In turn, this wider spacing reduces the number of lines which are required to be used at large angles in order to obtain a predetermined image resolution. Therefore, the image frame rate can be increased without decreasing image resolution. In particular, it has been found that acoustic lines spaced on a grid uniform in the reciprocal of the cosine of the steering angle produce satisfactory results.

In accordance with still another aspect of the present invention, the frame rate of an acoustic imaging system is increased by interpolating the signals generated by the transducers before they are provided to the beamforming circuit. More particularly, the angular separation between acoustic lines is increased to reduce the number of lines shot, thereby increasing the frame rate. The corresponding loss of resolution which would then normally occur is prevented by synthesizing the image information which would normally be contained in the missing acoustic lines by interpolating the existing data for angular positions between existing lines.

DETAILED DESCRIPTION OF PREFERRED EMBODIMENTS OF THE INVENTION

Figure 1:
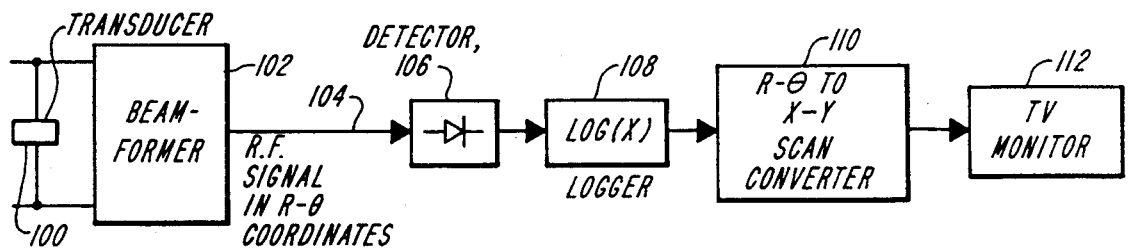
FIG. 1 is a simplified block electrical schematic diagram of a prior art acoustic imaging system.

FIG. 1 is a simplified block schematic diagram of a conventional phased-array acoustic imaging system. In particular, at the left side of the figure, an array of transducers 100 is connected to the input of a beamformer circuit 102 (only a single transducer is depicted for clarity). In general, the same array of transducers is used to both generate the transmit beam as well as receive the reflected pressure pulses. Although transducer 100 is schematically shown connected directly to beamformer 102, in actuality, transmit drivers and receive amplifiers would be connected between the transducers and the beamformer. The construction and connection of these latter circuits is well-known and, consequently, they are omitted from FIG. 1 for clarity.

The construction and operation of a beamformer circuit is also well-known to those skilled in the art and is discussed in more detail in the afore-mentioned U.S. Pat. No. 4,140,022. Briefly, the circuit contains a plurality of delay lines for selectively delaying transducer signals and a summing network to combine the delayed signals to produce an output electrical signal on line 104.

The beamformer output on lead 104 (as previously mentioned this output is in R-$\Theta$ coordinates) is then processed to generate the final X-Y signals which can be displayed on T.V. display 112. In particular, the output on lead 104 is detected and compressed prior to providing it to a scan converter which converts the R-$\Theta$ coordinates to X-Y coordinates. This additional processing is generally necessary because the beamformer output signals have a large dynamic range whereas a typical TV monitor can only display signals of a very limited dynamic range. Accordingly, the beamformer output signal on lead 104 is applied to a detector circuit 106.

Detector circuit 106 is typically an "absolute value" or "square-law" type detector which has been schematically illustrated in FIG. 1 as a diode. As the construction and operation of such detectors is well-known, detector 106 will not be discussed further herein, but the detector will be assumed to be an absolute value detector. The output of detector 106 is a signal which contains a DC level related to the magnitude of the input signal. This latter signal is provided to amplifier 108.

Amplifier 108 is used to reduce the dynamic range of the signal generated by detector 104 to the signal range that can be handled by the TV monitor 112. A typical device is a logarithmic amplifier called a "logger" which generates the output log(x) in response to an input signal x. However, other data compression devices are known and could be substituted for the logarithmic amplifier. Such devices might include any type of amplifier with a nonlinear transfer characteristic. The construction and operation of such data compression devices are conventional and will not be discussed further herein.

Figure 2:
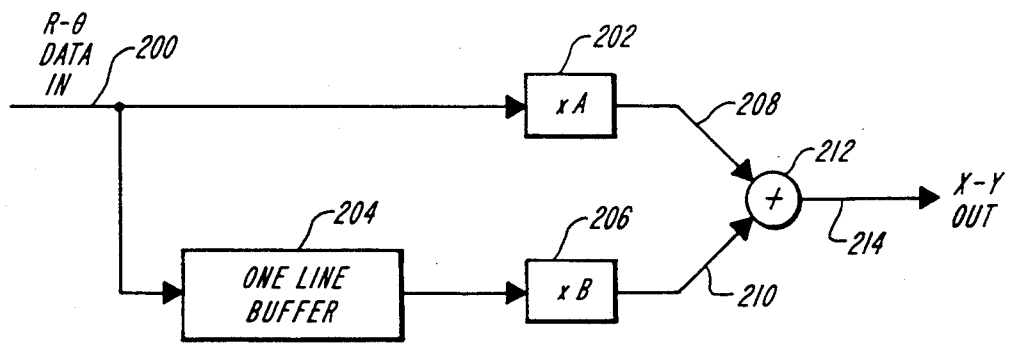
FIG. 2 is a more detailed block electrical schematic diagram of a the prior art scan converter circuit illustrated in FIG. 1.

The output of amplifier 108 is provided to scan converter 110 which converts the scan data in R-$\Theta$ coordinates to the X-Y coordinates needed for display. In general, the construction and operation of a scan converter schematically illustrated as box 110 is well-known. A more detailed block diagram is also shown in FIG. 2 which depicts the construction of the circuitry that performs the interpolation necessary to convert the R-$\Theta$ signals to X-Y signals.

R-$\Theta$ data on line 200 from data compression device 108 is provided directly to a scaling circuit 202 which multiplies the data by a preselected constant (A). Incoming data on input line 200 is also provided to a "one-line" buffer 204. In the case of analog data, buffer 204 may be a simple delay line which delays the analog information from line 200 for a time interval equal to the time delay between acoustic lines generated by the transducer array. Alternatively, if the incoming signals have been digitized, buffer 204 may be a temporary memory. In any case, the output of buffer 204 is provided to a second scaling device, 206, which scales the information by a second predetermined constant. Buffer 208 of scaling device 202 and output 210 of scaling device 206 are provided to a summing network 212 which produces the output 214. The buffer 204 allows the circuit to generate an interpolated value of the data for points occurring between scan lines. The output of scan converter 110 is provided to a TV monitor 112 for display.

Figure 3:
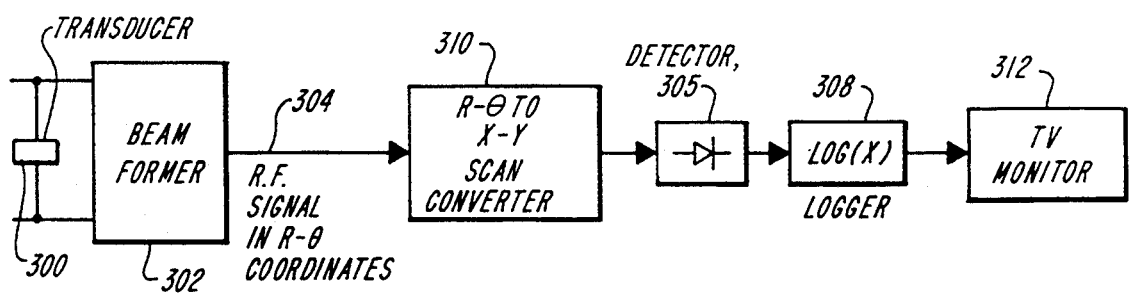
FIG. 3 is a simplified block electrical schematic diagram of an acoustic imaging system in which the apparatus has been reorganized in accordance with one aspect of the invention so that scan conversion is performed prior to signal detection and logging in order to increase the image resolution.

In accordance with the invention, the resolution of an acoustic image generated by an imaging system such as shown in FIG. 1 can be significantly increased by changing the signal processing order. In particular, as shown in FIG. 3, if scan conversion is performed on the data before detection and compression, the resolution of the image can be enhanced without increasing the number of scan lines. In particular, in FIG. 3, transducer 300 and beamformer 302 correspond to elements 100 and 102, respectively, shown in FIG. 1. The data signal generated by beamformer 302 on lead 304 is provided directly to scan converter 312 instead of detector 305 as in the prior art structure. The output of scan converter 310 is, in turn, provided to detector 305 and data compression device 308 and the output of amplifier 308 is provided to TV monitor 312 for display.

The effect of the inventive change in processing order can be explained by referring to FIGS. 4-11. FIGS. 4A and 4B illustrate a conventional manner of testing an acoustic imaging apparatus using a test "phantom" device in which "targets" formed by metal wires are embedded in a gelatin material that has an acoustic impedance approximately equal to that of water. FIGS. 4A and 4B illustrate two separate cross-sectional diagrams through two phantoms in a direction perpendicular to the wire axis. A wire car, be either "positive" (depicted as a "+" sign) indicating that it has an acoustic impedance greater than water or the wire can be "negative" (depicted as a "−" sign) indicating that it has an acoustic impedance less than water. These wires are then imaged by generating acoustic beams and sweeping them across the wires.

Figure 4A:
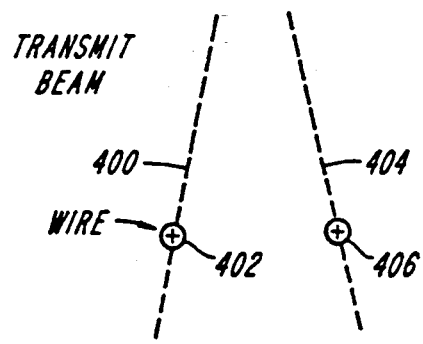
FIG. 4A is a cross-sectional view of an acoustic imaging test apparatus in which two "positive" target wires are embedded in gelatin material and used to illustrate the image improvement obtained with the apparatus of FIG. 3.
Figure 4B:
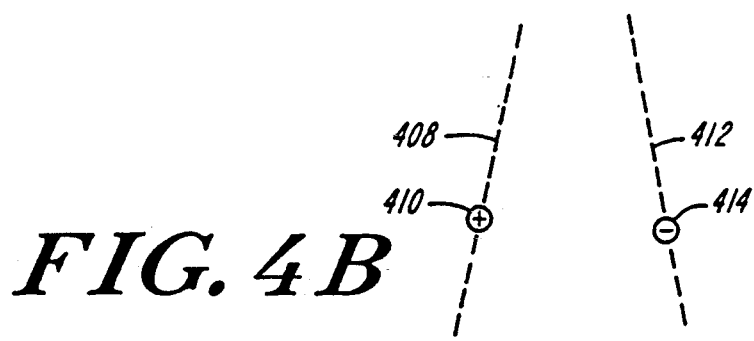
FIG. 4B is a cross-sectional view of an acoustic imaging test apparatus in which one "positive" target wire and one "negative" target wire are embedded in gelatin material and used together with FIG. 4A to illustrate the image improvement obtained with the apparatus of FIG. 3.

In FIG. 4A, two acoustic lines are shown interrogating, or locating the position of, two positive wires. Dotted line 400 illustrates an acoustic transmit beam shot to interrogate wire 402 and dotted line 404 represents a transmit beam used to interrogate wire 406. FIG. 4B illustrates a second phantom in which acoustic lines are shot to interrogate one positive and one negative wire. Line 408 represents a transmit beam used to interrogate positive wire 410 and line 412 is the transmit beam used to interrogate wire 414. During actual image formation many lines would be shot at predetermined angular increments. Lines 400,404, 408 and 412 represent only four of these lines.

Figure 5A:
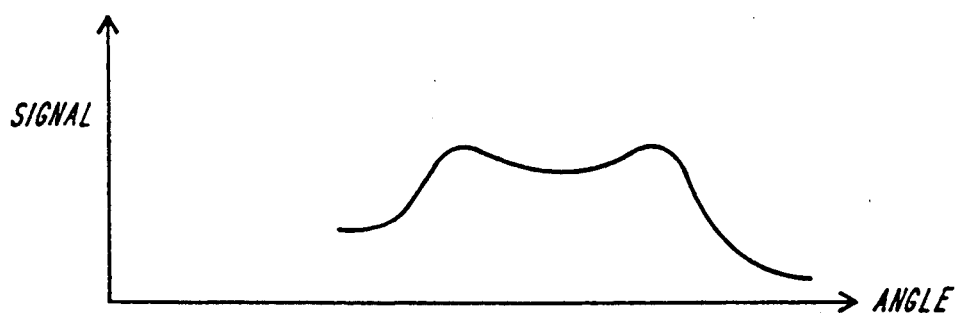
FIG. 5A illustrates the signal amplitude generated by the acoustic transducers versus receive beam angle for the test setup illustrated in FIG. 4A using the prior art imaging apparatus shown in FIG. 1.

FIGS. 5A-8B illustrate the intermediate and displayed signals resulting when the test phantoms shown in FIGS. 4A and 4B are imaged with the prior art system shown in FIG. 1. More particularly, FIGS. 5A and 5B illustrate two graphs of "continuous" signal amplitude vs. transmit beam angle for signals generated by a beamformer circuit for the two test phantoms illustrated in FIGS. 4A and 4B, respectively. These diagrams represent theoretical responses which would be expected if an infinite number of lines were shot. As shown in FIG. 5A, as the transmit angle is adjusted so that the acoustic line aligns with the wire in the position shown as line 400, the signal amplitude reaches a maximum. There are two maxima, one corresponding to each of the positive wires shown in FIG. 4A corresponding to transmit beams 400 and 404. In FIG. 5B, there is a positive maximum and a negative maximum corresponding to the positive and negative wires shown in FIG. 4B.

Figure 6A:
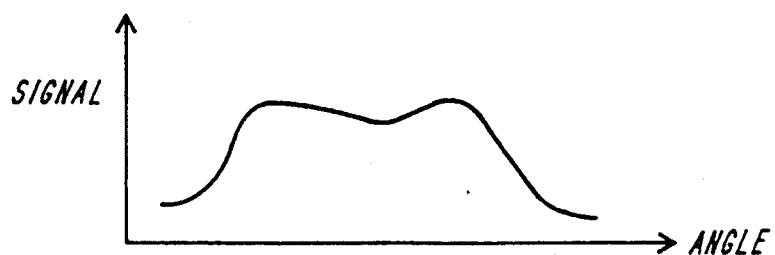
FIG. 6A illustrates a signal which results from the detection of the signal in FIG. 5A.
Figure 6B:
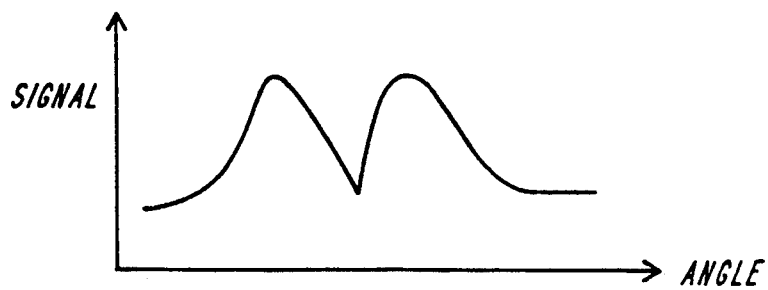
FIG. 6B illustrates a signal which results from the detection of the signal in FIG. 5B.

Assuming that the system shown in FIG. 1 is used to process the beamformer data, FIG. 6 shows the "continuous, signal which results from the output of a detector such as detector 106. As previously mentioned, this detector is an absolute value detector and thus the amplitude of the signal becomes positive or folded over the axis. In FIG. 6A, the detected signal is essentially the same as the beamformer output since the original signal is entirely positive. However, in FIG. 6B, the negative portion of the signal appears as a second positive maxima due to the squaring action of the detector.

Figure 7A:
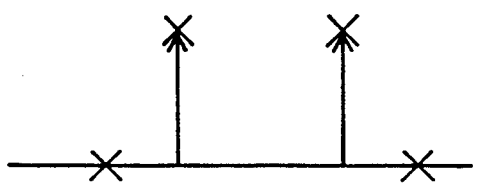
FIG. 7A illustrates a signal which results from sampling the signal in FIG. 6A.
Figure 7B:
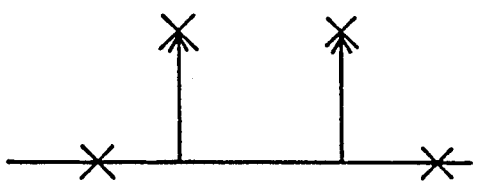
FIG. 7B illustrates a signal which results from sampling the signal in FIG. 6B.

However, an actual imaging system does not shoot an infinite number of lines, but uses a finite number of lines to generate the image. The effect of using a finite number of lines is to convert the signal into a sampled data signal. FIG. 7A illustrates what such a signal would look like if only four lines were used to interrogate the test phantom shown in FIG. 4A. The four lines shot correspond to lines 400 and 404 illustrated in FIG. 4A and two additional lines, shot on either side of lines 400 and 404. FIG. 7B illustrates a four line signal for the phantom shown in FIG. 4B. The two vertical lines in each of FIGS. 7A and 7B correspond to the acoustic lines Which intercept the wires. The sampled signals are effectively the amplitude of the continuous signals shown in FIGS. 6A and 6B at the sampling angles.. Since the continuous signals exhibit only positive maxima in both FIG. 6A and 6B, the sampled signals in FIGS. 7A and 7B are exactly the same.

Figure 8A:
FIG. 8A illustrates a signal which results from scan conversion or linear interpolation of the signal in FIG. 7A.
Figure 8B:
FIG. 8B illustrates a signal which results from scan conversion or linear interpolation of the signal in FIG. 7B.

In order to display the sampled signals, a scan conversion is done in which the sampled version of the signals is linearly interpolated to produce the final output. This interpolated output is shown in FIGS. 8A and 8B and is identical for both of the test phantoms. Thus, although the test phantoms shown in FIGS. 4A and 4B are different, the resulting images are the same because the phase information has been discarded during the signal processing procedure.

Figure 9A:
FIG. 9A illustrates a signal which results from sampling the signal in FIG. 5A in accordance with the apparatus shown in FIG. 3.
Figure 9B:
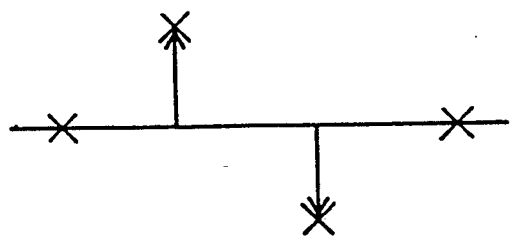
FIG. 9B illustrates a signal which results from sampling the signal in FIG. 5B in accordance with the apparatus shown in FIG. 3.

FIGS. 9A-10B illustrate the intermediate and displayed signals which are generated when the inventive apparatus shown in FIG. 3 is used to process the beamformer signals in particular, the output of beamformer 302 as shown in FIG. 3 is now directly applied to scan converter 310. In this case, interpolation takes place before detection. As shown in FIG. 9A, in the sampled signal version of the continuous signals shown in FIGS. 5A and 5B, both of the positive signal maxima illustrated in FIG. 5A result in positive samples. However, in FIG. 9B, the positive and negative maxima in FIG. 6B result in one of the samples being positive while the other sample is negative due to the negative maximum shown in FIG. 6B.

Figure 5B:
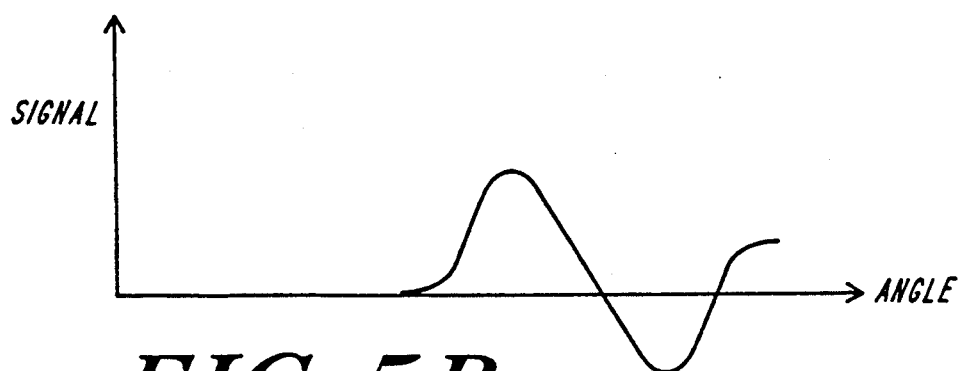
FIG. 5B illustrates the signal amplitude generated by the acoustic transducers versus receive beam angle for the test setup illustrated in FIG. 4B using the prior art imaging apparatus shown in FIG. 1.
Figure 10A:
FIG. 10A illustrates a signal which results from scan conversion or linear interpolation of the signal in FIG. 9A.
Figure 10B:
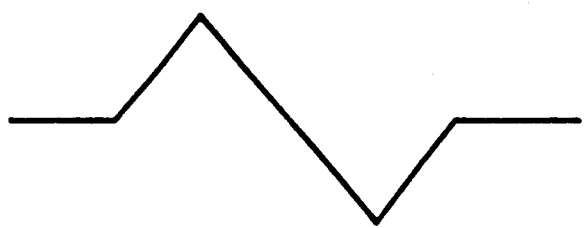
FIG. 10B illustrates a signal which results from scan conversion or linear interpolation of the signal in FIG. 9B.

As shown in FIGS. 10A and 10B, the linearly interpolated output of scan converter 310 is now different for the two test phantoms. When the signal shown in FIGS. 10A and 10B is detected resulting in the signals shown in FIGS. 11A and 11B, the resulting signal includes a minimum 1102 resulting from the lack of signal between the two wires as illustrated in FIG. 5B. The output of the detector is displayed in the inventive system.

Figure 11A:
FIG. 11A illustrates a signal which results from the detection of the signal in FIG. 9A.
Figure 11B:
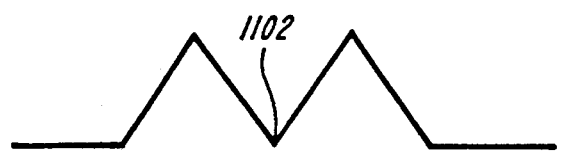
FIG. 11B illustrates a signal which results from the detection of the signal in FIG. 9B.

Thus, as can be seen by comparing FIGS. 11A and 11B with FIGS. 8A and 8B, reversing the order of scan conversion and detection generates an image with additional information because the phase information present in the original object is not lost during processing. It can easily be seen that, for targets having an arbitrary phase difference of θ, the depth of the interpolated null produced by the inventive imaging system is cos (⊖/2) and that the resulting picture contains all the phase information present at the beamformer summing node. Another way of stating this is that, from the nulls displayed in the final image, the phase of the signals at the beamformer summing node can be mathematically determined.

Figure 12:
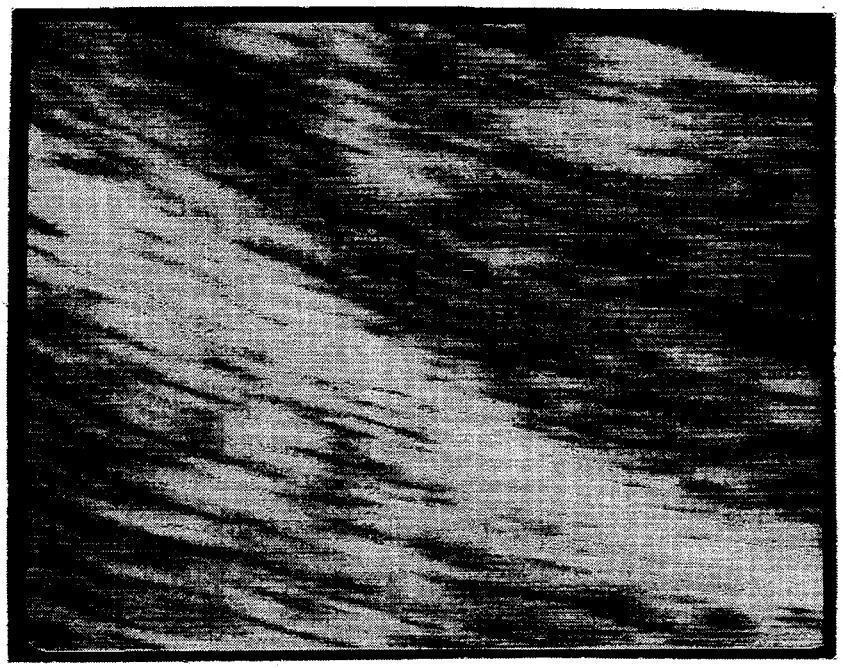
FIG. 12 shows a magnified image of a section of heart muscle generated using a conventional Ultrasonic imaging system.
Figure 13:
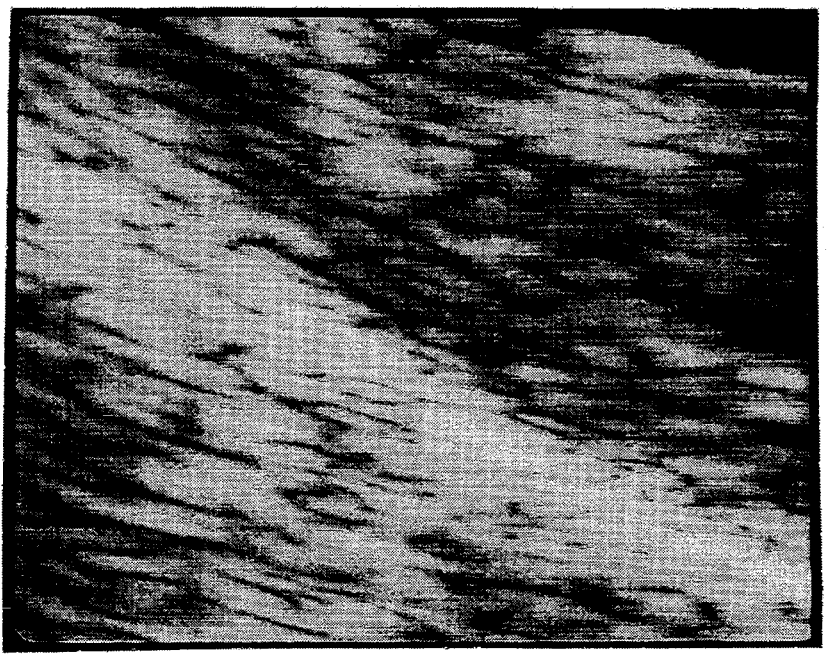
FIG. 13 shows a magnified image of the section of heart muscle shown in FIG. 11 generated using a the inventive ultrasonic imaging system.

A comparison of FIGS. 12 and 13 illustrates the improvement in image quality which results from using the inventive apparatus and method. In particular, FIG. 12 shows a magnified image of a section of heart muscle. The image was generated using a conventional ultrasonic imaging system sold by Hewlett-Packard Company, 3000 Minuteman Road, Andover, Mass. 01810, under the name "PRISM" using a 3.5 MHz ultrasonic frequency and an array with 128 transducers with a 0.75° line spacing. With this conventional system, detection occurred before scan conversion as shown in FIG. 1.

FIG. 13 uses the identical apparatus discussed above with the exception that detection is performed after scan conversion in accordance with the system shown in FIG. 3. In FIG. 13, each of the bright muscles is outlined with a clearly defined dark circle corresponding to the null between fibers thereby more clearly defining the muscles as compared to the conventional image as shown in FIG. 12.

Conventionally generated images, such as that shown in FIG. 12, often exhibit a recurring artifact which shows up as bright radial streaks. It has been found that these streaks are a result of the scan conversion interpolation which is performed between actual data points to produce the final display. More particularly, it has been found that the conventional linear interpolation scheme used in scan conversion causes a lower effective gain when a data point necessary for display falls between two R-⊖ data points from two different acoustic lines. In this case, the prior art interpolators (such as that illustrated in FIG. 2) construct the necessary data point by scaling the two available data points by means of multipliers 202 and 206 where the coefficients, A and B, are selected such that A+B=1.

A linear interpolation scheme such as this is simple to implement and results in a smooth interpolation which creates no effective D.C. level shift. However, in accordance with another aspect of the invention, it has been found that the theoretical continuous angular response of an object located between acoustic lines which would result if additional lines were shot is approximately 1.8 db higher than the response calculated by linearly interpolating the response data between the two data points. In particular, in accordance with the invention, an interpolation which uses values corresponding to a sinc function is preferred instead of linear interpolation.

Figure 14:
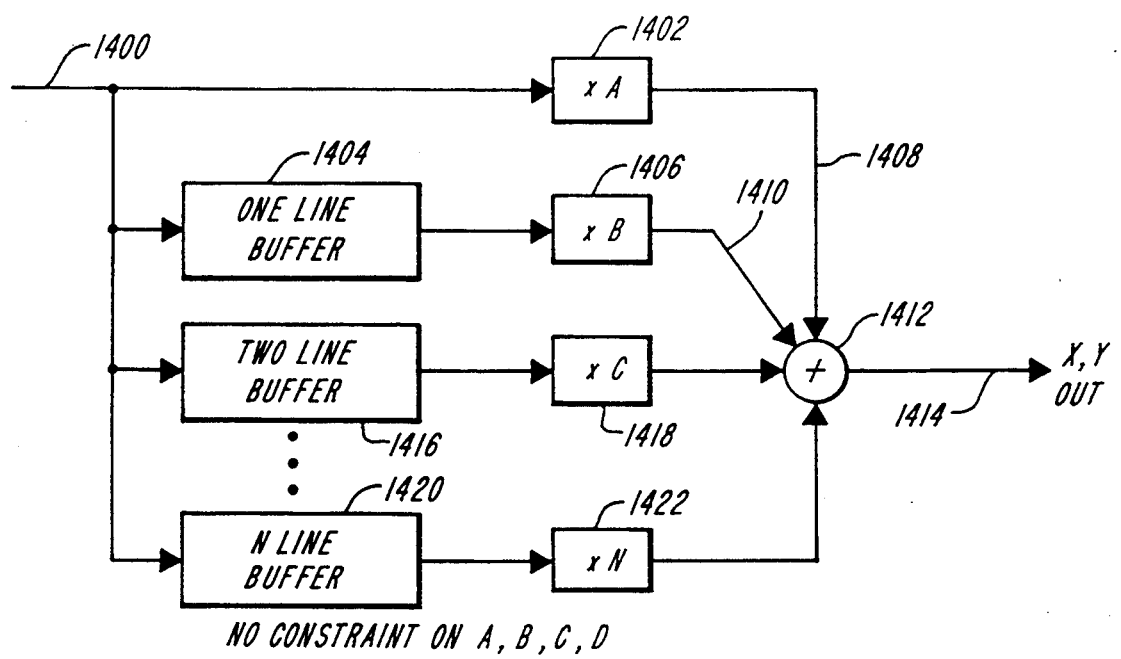
FIG. 14 is a block schematic diagram of a preferred circuit structure for performing scan conversion interpolation.

A preferred structure is shown in FIG. 14. Input data on line 1400 is applied directly to multiplier 1402 where it is multiplied by the predetermined constant A and applied to the summing point 1412. Input 1400 is also applied to a one line buffer 1404 and the output of buffer 1404 is applied to a multiplier 1406 and, via output 1410, to summing point 1412. Additional buffers, two of which are shown as buffers 1416 and 1420, may also be provided. The output of these buffers are provided to multipliers 1418 and 1422, respectively. The outputs of the multipliers are, in turn, applied to the summing point 1412. However, in the inventive arrangement, the coefficients A, B, C . . . N do not sum to unity. Instead, the coefficients are adjusted so that they assume the values of an ideal sinc function ((sin x)/x).

In particular, in accordance with the invention, the scan conversion is treated as equivalent to a classic Nyquist sampling-reconstruction problem. Specifically, it can be shown by Fourier optics that the angular spatial frequencies in the acoustic signals generated by any transducer array are absolutely bandlimited. Consequently, as long as the classic Nyquist criteria are met, it is possible to acoustically sample an object at discrete angle increments and to reconstruct the resulting image with an ideal Nyquist filter.

Since such an ideal filter has a sinc function impulse response, the most accurate reconstruction will occur when a sinc function is used during the scan conversion for interpolation.

Practically, it is not possible to generate an ideal sinc function response, since this would require an infinite number of delays and multipliers. However, it has also been found that it is not necessary for the sinc function interpolator to be absolutely ideal. Instead, a curve can be used which approximately corresponds to the main lobe of the sinc function. This curve replaces the triangle function that is normally used in the prior art.

For example, in order to calculate a data signal at a point centered between two known data points, it has been found that, instead of the prior art method of multiplying each of the two data points by 0.5 and summing the results, the previously-mentioned artifacts can be reduced by multiplying each data point by 0.58 and summing the results. Since the coefficients do not sum to one, the inventive interpolation scheme does introduce a DC level into the signal. However, scan conversion removes the DC component before detection thereby eliminating any potential problems.

More particularly, the following equation can be used to estimate the image field at an angle ⊖ from a plurality of known data points 1 . . . N:

$$\text{signal }(\Theta) = \Sigma a(i, \Theta - \Phi) \text{ signal }(\Phi = (i - N/2)\Delta\Phi)$$

where $\Delta\Phi$ = spacing between discrete angles and $\Phi = \Delta\Phi \text{int}(\Phi/\Delta\Phi)$ is the largest discrete angle less than or equal to $\Phi$. The function $a(i, \Theta - \Phi)$ designates a continuous interpolation function. As the number of data points N used in the interpolation becomes larger, the interpolation function $a(i, \Theta - \Phi)$ approaches a sinc function:

$$\text{SIN}\left(\pi\left(\frac{(\theta - \phi)}{\Delta\phi} + i\right)\right) / \left[\pi\left(\frac{(\theta - \phi)}{\Delta\phi} + i\right)\right]$$

Figure 15:
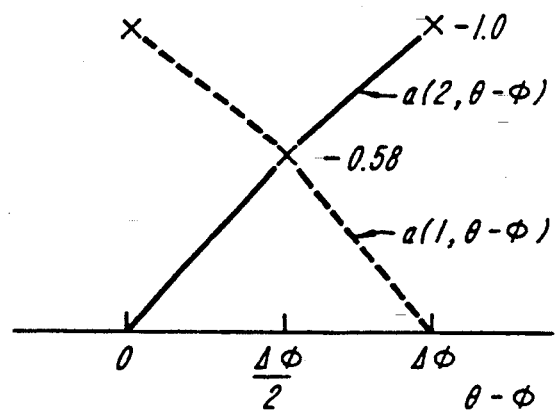
FIG. 15 is a graphical diagram illustrating an interpolation function in accordance with one aspect of the invention.

However, if the interpolation is performed using a small number of points, it is necessary to chose a function $a(i, \Theta - \Phi)$ empirically. For example for N=2 (two-point interpolation) the curve shown in FIG. 15 was found to give satisfactory results and shows the 0.58 value used in the previous example. When this value was used in the two-point interpolation, the radial line artifacts present in the prior art image were greatly reduced.

Figure 16:
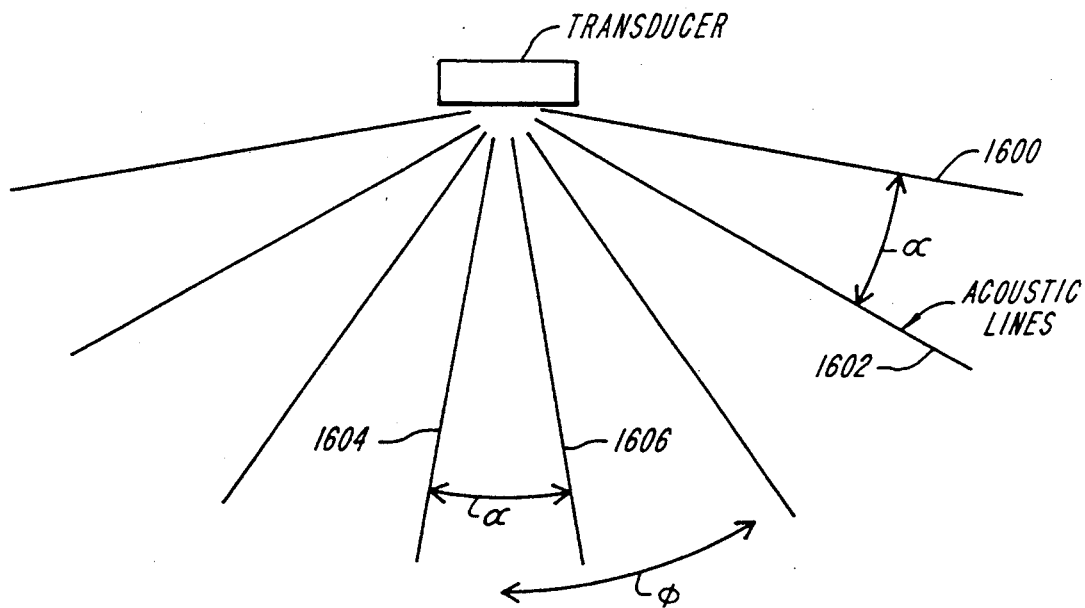
FIG. 16 is a schematic illustration indicating a prior art method of shooting acoustic lines at equal angular increments.

In accordance with another aspect of the invention, it has been found that the imaging frame rate can be increased without loss of resolution by using nonuniform angular sampling. In particular, prior art imaging systems use uniform angular sampling as shown in FIG. 16 in which the angular increment $\alpha$ between acoustic lines is constant over the entire 180° image sector so that the angle (called a steering angle) for the nth acoustic line ($\Phi_n$), $\Phi_n = n\alpha$. For example the angular spacing between transmit lines 1600 and 1692 (schematically illustrated as lines in FIG. 16) is the angle $\alpha$. This angle is the same as the angle $\alpha$, between two other lines 1604 and 1606. Thus, the angular spacing is independent of the steering angle, $\Phi$. In accordance with another aspect of the invention, it has been found that the prior art uniform angular sampling over samples the object for large steering angles thereby resulting in unnecessarily low frame rates. More specifically, for large steering angles, the effective "aperture" of the phased array can be reduced by the cosine of the steering angle due to the angles at which the transmit and receive beams propagate. As the aperture is reduced in size, the effective width of the transmit and receive means increases. Therefore, a larger angular spacing between acoustic lines can be used to obtain the same resolution. By reducing the number of lines shot at large angles, the overall number of lines can be reduced to obtain an image with a predetermined resolution.

Figure 17:
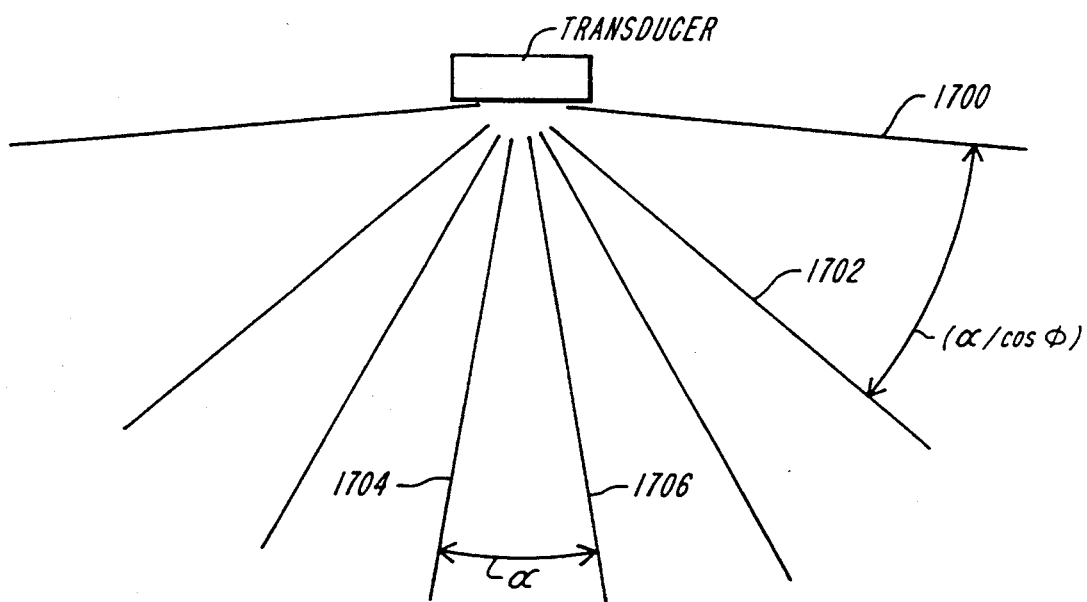
FIG. 17 is a schematic illustration of a scan sequence in accordance with the present invention in which the scan lines are shot at unequal intervals.

More particularly, it has been found that the acoustic lines can be spaced on a grid which is uniform in the reciprocal of the cosine of the steering angle so that the steering angle for the nth acoustic line is: $\Phi = \sin^{-1}(N\alpha)$. This method results in the acoustic line spacing shown in FIG. 17 and allows the effective frame rate to be increased. As shown in FIG. 17, if the spacing between lines 1704 and 1706 is $\alpha$, then, at large steering angles, $\Phi$, the angular spacing between lines is increased by $1/\cos \Phi$ as the spacing shown between lines 1700 and 1702 is $\alpha/\cos \Phi$.

In accordance with another aspect of the invention, it is also possible to reduce the number of acoustic lines, and thereby increase the frame rate, by, prior to beamforming, synthesizing acoustic information from linear combinations of the data available for acoustic lines which are shot. In accordance with Nyquist sampling theory, there exists a maximum angular spacing between the lines to insure no loss of spatial information. More particularly, the maximum allowed angular spacing between transmit lines, $\alpha_t$, can be derived by using Fourier optical and the spatial Nyquist sampling theorem and is given by:

$$\alpha_t = \frac{1.0 \text{ radians}}{\text{(transmit aperture width in wavelengths of the highest temporal frequency component)}}$$

As an example, the latter formula, when used with a conventional ultrasonic imaging system sold by Hewlett-Packard Company, 3000 Minuteman Road, Andover, Mass. 01810, under the name "PRISM" using a 3.5 MHz ultrasonic frequency and an array with 128 transducers (used for both transmit and receive) spaced one-half wavelength apart given $\alpha_t = 0.90$ degrees.

With the above-mentioned system, a receive beam is formed at each transmit beam angle by delaying an summing signals from a number of receive elements in a manner previously described. Even though the transmit line spacing is given by the above equation, the receive lines must be separated by a smaller angular spacing $\alpha_r$ given by:

$$\alpha_r = \frac{1.0 \text{ radians}}{\text{(transmit aperture width)} + \text{(receive aperture width)}}$$

For the example given immediately above, $\alpha_r = 0.45$ degrees. This difference between the required number of transmit and receive lines allows the use of an inventive method and apparatus in which acoustic lines are shot at the spacing determined by $\alpha_t$ and interpolation is performed on the signals from each receive transducer to synthesize the signals that would have been available if the actual line spacing had been $\alpha_r$.

This method works because, prior to beamforming, each individual receive element acts like its own system with a receive aperture width of near-zero. Therefore, to adequately sample the signals on each individual receive element, the transmit angular separation $\alpha_t$ can be used because $\alpha_r$ becomes equivalent to $\alpha_t$ when the receive aperture is set to zero width.

Figure 18:
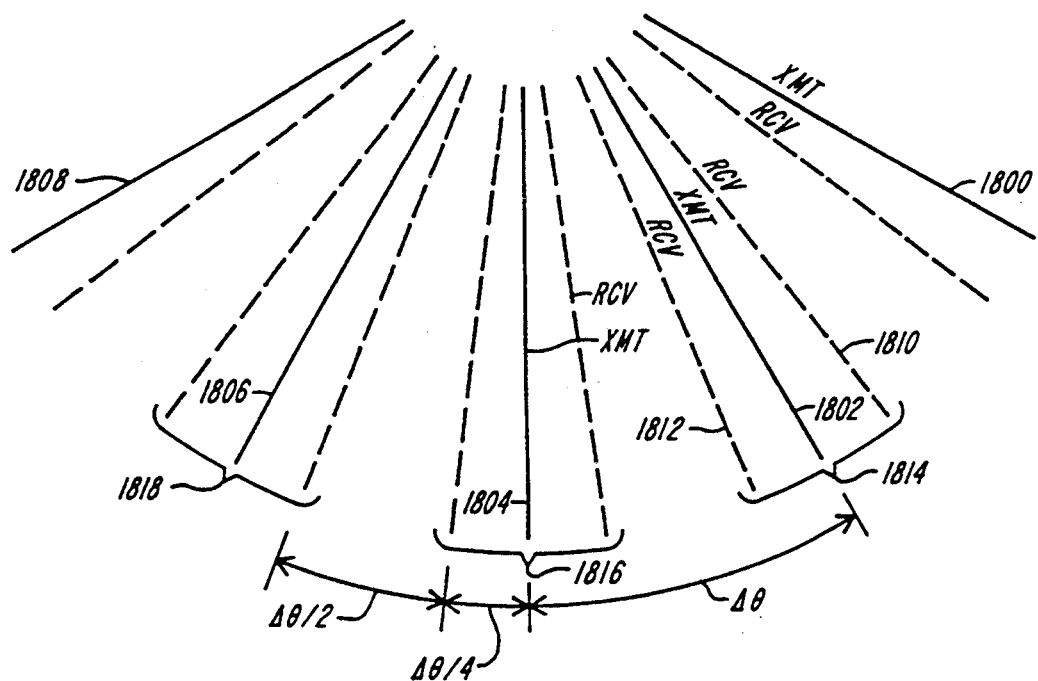
FIG. 18 illustrates a method for reducing system frame rate by synthesizing receive information prior to beamforming.

The simplest interpolation construction involves the synthesis of two receive beams for each transmit beam that is actually shot. The synthesis is performed so that the synthesized beams are "received" on each side of a central transmit beam as shown in FIG. 18. Two beamformers are used to reconstruct the signals so that the beamformer outputs appear as if two transmit beams were shot. FIG. 18 schematically illustrates a portion of a sector with transmit and receive beams illustrated as lines (the beam angular spacing is greatly exaggerated in FIG. 18 for clarity). The solid lines 1800–1808 represent the transmit beams which are actually shot. The dotted lines represent receive beams which are synthesized from the received information using circuitry as described below. In accordance with the invention, the received signals can be used to synthesize two receive beams as if two transmit beams had been shot even though they actually were not. For example, synthesized receive beam illustrated as line 1810 can be generated from the received information from transmit beam 1802 by means of delays and linear combinations. In a similar manner, synthesized beam 1812 can also be generated from received information generated by transmit beam 1802, resulting a pair of beams identified by bracket 1814 being generated from a single transmit beam. The synthesized beams are arranged symmetrically around the transmit beam from which they are generated. More specifically, if the transmit beams have an angular spacing of $\Delta\Theta$, then the received beams are generated at an angular spacing of $\Delta\Theta/4$ on either side of the associated transmit beam. The spacing between the synthesized receive beams and the transmit beam spaces the synthesized receive beams at equal angular increments of $\Delta\Theta/2$. In a similar manner, transmit beam 1804 can be used to generate two synthesized beams identified by bracket 1816. Synthesized beams identified by bracket 1818 are, in turn, generated from transmit beam 1806.

Figure 19:
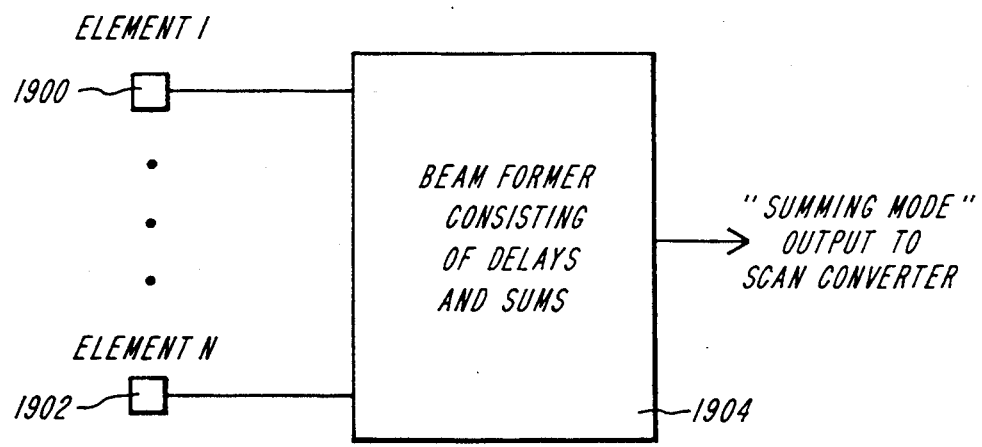
FIG. 19 is a schematic diagram indicating a conventional connection of transducer elements to the beamformer.

In order to synthesize receive beams, the conventional receiving circuitry must be modified. In a conventional scanning system as shown in FIG. 19, a plurality of receive transducer elements, designated as elements 1 . . . N, are used to construct a receive beam.

For simplicity, only two elements 1900 and 1902 are shown. Each element is connected directly to a beamformer 1904 which constructs the receive beam by appropriately weighting and summing the transducer output signals.

Figure 20:
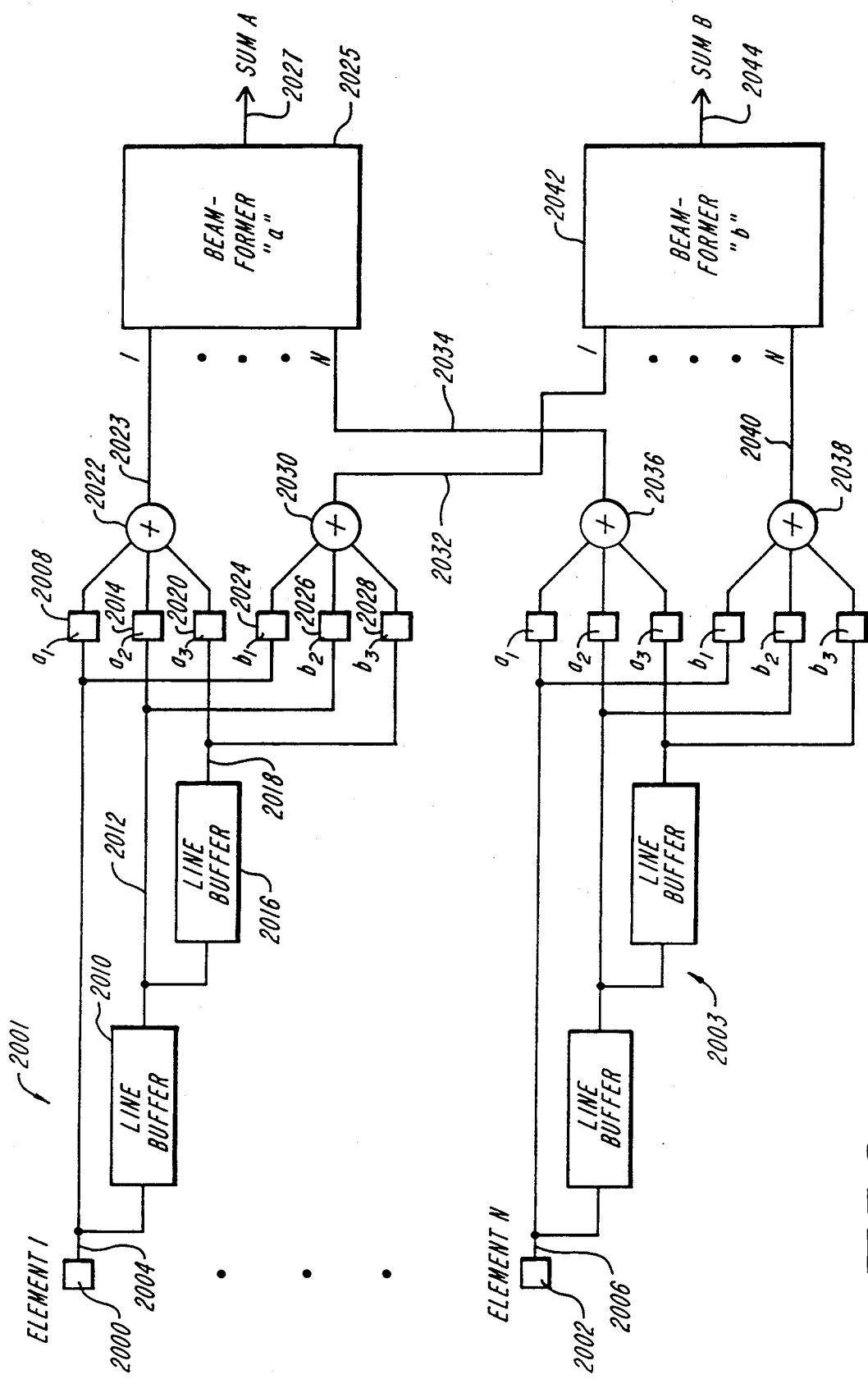
FIG. 20 is a schematic diagram in accordance with another aspect of the present invention in which the acoustic elements are connected to a plurality of beamformers by means of interpolation circuits.

FIG. 20 schematically illustrates circuitry which can be used to synthesize additional line information from existing transducer receive outputs. Each of transducer elements (of which elements 2000 and 2002 are shown) is connected to two beamformers 2025 and 2042 through an interpolation circuit of which interpolation circuits 2001 and 2003 are shown. As each of the interpolation circuits are identical, only circuit 2001 will be discussed in detail. Although only two synthesized beams are generated, in general, the transducer output information could be used to synthesize three or more receive lines as will be discussed below. The extension of the circuitry for three or more lines is straightforward.

More specifically, the output of element 2000 on lead 2004 is provided to a pair of line-generator circuits; the first circuit consists of multipliers 2008, 2014, and 2020, and summing junction 2022, and the second line-generator circuit consists of multiplier 2024, 2026, and 2028, and summing junction 2030. In the first line-generator circuit, output 2004 is provided directly to multiplier 2008 and to the input of line buffer 2010. Line buffer 2010 delays the output 2004 for a time period equivalent to the transmit and receive time of the system so that the output 2012 of line buffer 2010 comprises the output of transducer 2000 for the previous acoustic line.

Output 2012 is, in turn, provided to a second line buffer 2016, so that the output of this latter buffer on lead 2018 consists of the output 2004 of transducer 2000 delayed by two line time periods. The outputs, 2012 and 2018, of line buffers 2010 and 2016 are respectively provided to multipliers 2014 and 2020.

Multipliers 2008, 2014, and 2020 are supplied with constants $a_1$, $a_2$ and $a_3$, respectively, that scale the transducer and line buffer outputs. Each multiplier provides a scaled output to a summing junction 2022. The scaling and summing synthesizes a "new" receive value on the output 2023 of summing junction 2022 from the transducer output 2004 from the receive information available for three consecutive transmit lines. This synthesized output is provided to one input of a convention beamformer 2025.

The output of transducer 2000 on line 2004 and the outputs 2012 and 2018 of line buffers 2010 and 2016 are also provided to three additional multipliers: 2024, 2026 and 2028. These latter multipliers are provided with three different scaling constants, $b_1$, $b_2$ and $b_3$, and the scaled outputs are applied to summing junction 2030 in order to generate an additional synthesized output. If the "a" and "b" constants differ, the second synthesized output will differ from the first synthesized output. The latter synthesized output on line 2032 of summing junction 2030 is provided to the first input of a second conventional beamformer 2042.

Beamformer 2025 generates an output on lead 2027 and beamformer 2042 generates an output on lead 2044. These outputs can be stored and processed as if twice as many lines were shot than the actual number of lines.

A similar interpolation circuit is provided for the output of each transducer element. For example, interpolation circuit 2003 is provided at the output of transducer element 2002. Each interpolation circuit generates two synthesized lines. One of these lines is provided to one input of beamformer 2025 and the other line is provided to one input of beamformer 2042. For example, the outputs of interpolation circuit 2003 generated by summing junction 2034 and 2038 are provided via lines 2036 and 2040 as the "n" input to beamformer 2025 and 2042.

One problem with the circuit shown in FIG. 20 is that two line-generating circuits must be connected to each transducer output resulting in a total of 2N line-generator circuits. Consequently, the circuit can be expensive.

Figure 21:
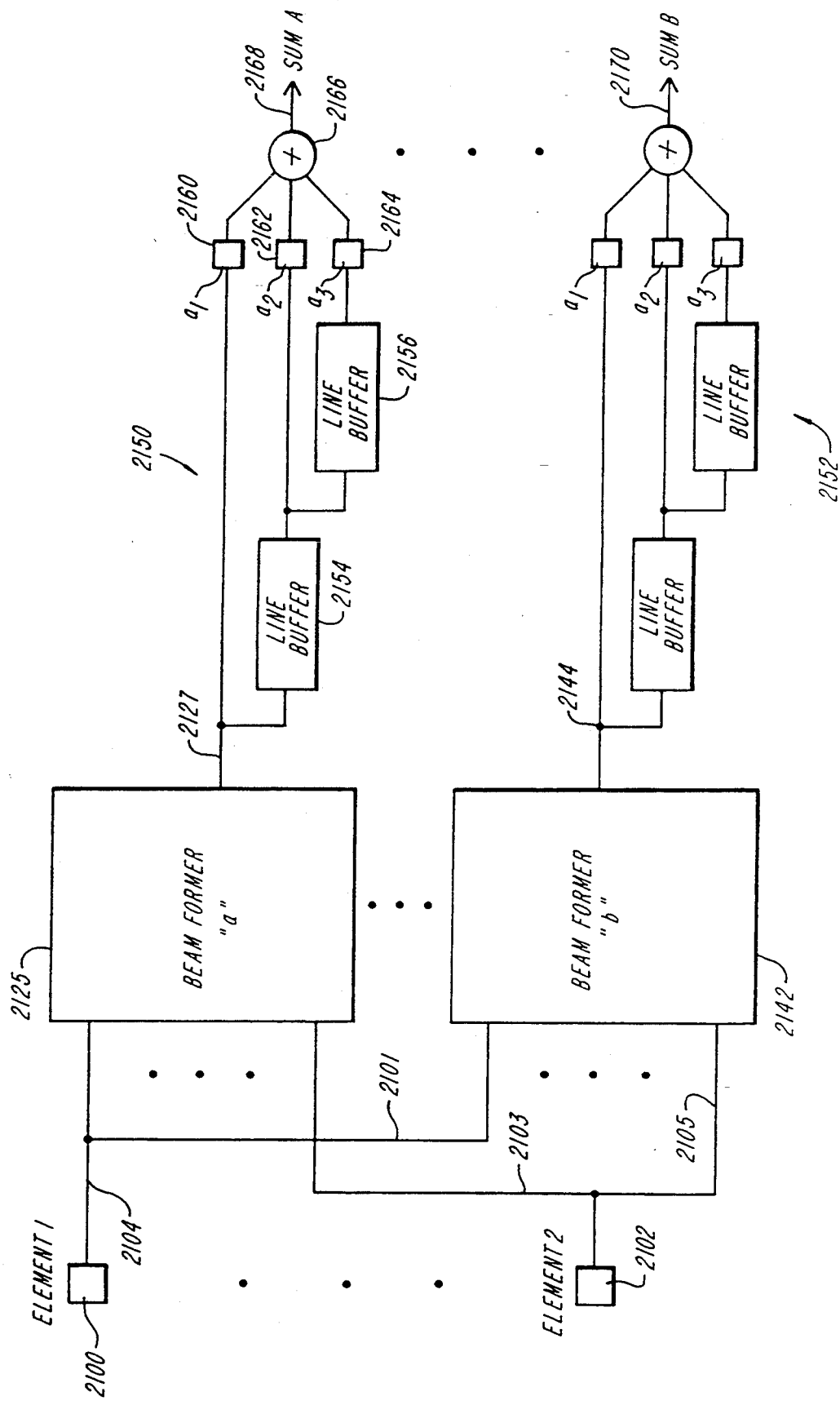
FIG. 21 is a modification of the circuitry shown in FIG. 20 in which a plurality of interpolation circuits is connected to the output of a plurality of beamformers in order to reduce the number of acoustic scan lines necessary to reconstruct the image.

FIG. 21 shows an alternative embodiment in which interpolation is performed after beamforming in order to reduce the number of line-generating circuits required. In particular, the outputs of the N receive transducer elements (of which elements 2100 and 2102 are shown) are provided to two beamformers 2125 and 2142. More particularly, the output of transducer element 2100 is provided, via lead 2104, to beamformer 2125 and, via lead 2101, to beamformer 2142. In a similar manner, the output of transducer 2102 is provided, via lead 2103, to beamformer 2125 and, via lead 2105, to beamformer 2142.

The output of each of the beamformers 2125 and 2142 is, in turn, provided to an interpolation circuit. For example, the output of beamformer 2125 on lead 2127 is provided to interpolation circuit 2150. In a similar manner, the output 2144 of beamformer 2142 is provided to interpolation circuit 2152. As interpolation circuits 2150 and 2152 are essentially equivalent, only interpolation circuit 2150 will be described in detail.

Interpolation circuit 2150 consists of two line buffers 2154 and 2156, three multipliers 2162–2164 and a summing junction 2166. Multiplier 2160 multiplies the output of beamformer 2125 by a predetermined constant $a_1$ and provides the scaled output to summing junction 2166. The output of beamformer 2125 is also applied to line buffer 2154 which, as previously described, delays the output for a time period equal to the time necessary to shoot one acoustic line. The output of line buffer 2154 on lead 2158 is provided to multiplier 2162 wherein it is multiplied by a second constant $a_2$ and applied to summing junction 2166. The output of line buffer 2154 on lead 2158 is also provided to line buffer 2156 where it is delayed by another time period equal to an acoustic line time duration. The output of line buffer 2156 is, in turn, applied to multiplier 2164 where it is multiplied by a constant $a_3$. The scaled output provided to summing junction 2166.

By suitably adjusting the constants $a_1-a_3$, a sum can be formed at the output 2168 of summing junction 2166 which is the interpolated output of beamformer 2125 constructed from three successive acoustic line scans.

Interpolator 2152 operates in a similar manner to generate a second interpolated output on lead 2170. The constants and the multipliers in interpolator 2152 are adjusted to the same values of the multipliers in interpolator 2150. This scheme functions in a similar manner to that shown in FIG. 20 with the exception that only two interpolation circuits are necessary instead of the 2N interpolation circuits necessary in FIG. 20.

When two receive beams are synthesized for each transmit beam, there will be a signal-to-noise ratio loss because the synthesized transmit beams do not return along the path taken by the transmit beam as shown in FIG. 18. There also may be a "checkerboard" artifact produced since all synthesized receive lines don't have identical beam profiles. In order to eliminate the signal-to-noise penalty and possible artifacts, three beamformers can be used to generate three outputs from the received data from each actual transmit beam. The beamformer outputs are preferably generated at the sequence of angles given in the following table for each transmit angle:

TABLE I

| Transmit Angle | Beamformer #1 receive angle | Beamformer #2 receive angle | Beamformer #3 receive angle |
|---|---|---|---|
| • | • | • | • |
| • | • | • | • |
| • | • | • | • |
| 0 | 0 | $-\Delta\Theta/2$ | $\Delta\Theta/2$ |
| $\Delta\Theta$ | $\Delta\Theta$ | $\Delta\Theta/2$ | $3\Delta\Theta/2$ |
| $2\Delta\Theta$ | $2\Delta\Theta$ | $3\Delta\Theta/2$ | $5\Delta\Theta/2$ |
| $3\Delta\Theta$ | $3\Delta\Theta$ | $5\Delta\Theta/2$ | $7\Delta\Theta/2$ |
| • | • | • | • |
| • | • | • | • |
| • | • | • | • |

In order to synthesize round-trip receive line information, the outputs of each beamformer are stored in a memory and the stored outputs are then combined to generate the synthesized receive beams. A preferred combination is given in Table II:

TABLE II

| Synthesized round-trip angle | Linear combination used to synthesize round-trip beam |
|---|---|
| • | • |
| • | • |
| • | • |
| 0 | R1(0) |
| $\Delta\Theta/2$ | $0.68*[R2(\Delta\Theta) + R3(0)]$ |
| $\Delta\Theta$ | $R1(\Delta\Theta)$ |
| $3\Delta\Theta/2$ | $0.68*[R2(\Delta\Theta) + R3(\Delta\Theta)]$ |
| $2\Delta\Theta$ | $R1(2\Delta\Theta)$ |
| • | • |
| • | • |
| • | • | where Rn(x) is the stored output signal generated by beamformer n from a transmit beam at steering angle x. An examination of Table II indicates that the synthesized round-trip receive beam data is generated by averaging data from transmit beams shot at two different steering angles. Effectively, the combination of data from two transmit beams makes the system appear as if a third transmit beam was actually shot between actual transmit beams.

Figure 22:
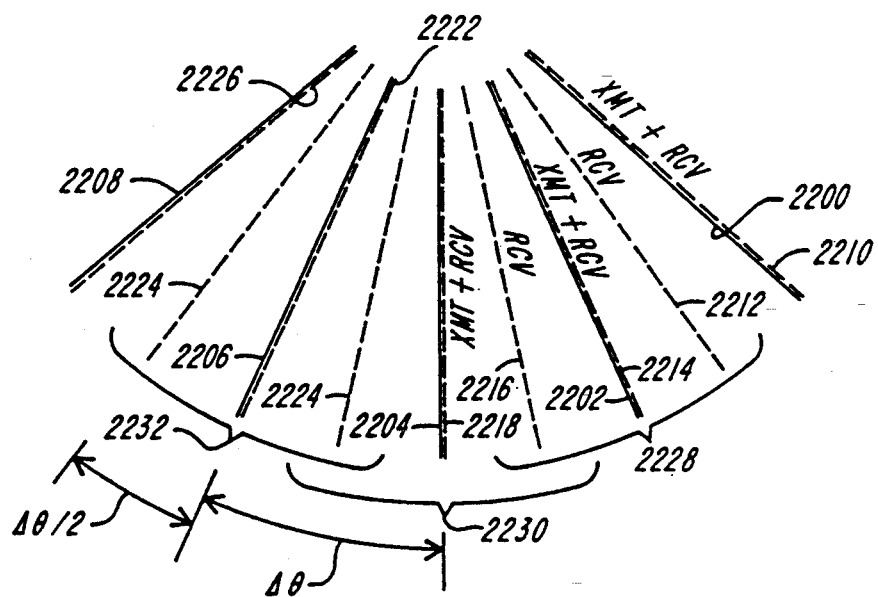
FIG. 22 is a schematic illustration of synthesized receive beam information in relation to transmit beam information using circuitry such as that shown in FIGS. 20 and 21 and received information from three parallel beams.

The synthesized line information is illustrated in relation the original transmit beams in FIG. 22. As with FIG. 18, the actual transmit beams are shown in FIG. 22 as solid lines 2200–2208. The synthesized receive beams are shown in dotted lines. In accordance with Table II, the data from two transmit beams is used to synthesize one of the receive beams. For example, a receive beam 2210 is generated from data from transmit beam 2200 and receive beam 2214 is generated from data from transmit beam 2202. Receive beam 2212 is generated by combining data from transmit beams 2200 and 2202. In a similar manner, receive beams 2218, 2222 and 2226 are generated from transmit beams 2204, 2206 and 2208, respectively. Receive beams 2216, 2220 and 2224 are generated from transmit beams pairs 2202, 2204; 2204, 2206 and 2206, 2208, respectively. Brackets 2228, 2230 and 2232 identify receive beam information for groups of three beams which are generated in parallel.

In this latter synthesis, there is no loss in signal-to-noise ratio since the synthesized receive beams are in perfect alignment with either actual transmit beams or "synthesized" transmit beams. In fact, there is a slight signal-to-noise ratio gain due to a resolution-signal-to-noise ratio tradeoff. However, as in the two parallel beam scheme, there may be a "checkerboard" artifact since all round-trip beams don't have the same beam profile. In addition, this scheme may be sensitive to object motion since it averages data generated by transmit lines shot at different times.

It is also possible to use four parallel beamformers to generate four parallel outputs at the transmit and receive angles shown in Table III:

TABLE III

| Transmit Angle | Beamfmr #1 rcv angle | Beamfmr #2 rcv angle | Beamfmr #3 rcv angle | Beamfmr #4 rcv angle |
|---|---|---|---|---|
| • | • | • | • | • |
| • | • | • | • | • |
| • | • | • | • | • |
| 0 | $-3\Delta\Theta/4$ | $-\Delta\Theta/4$ | $\Delta\Theta/4$ | $3\Delta\Theta/4$ |
| $\Delta\Theta$ | $\Delta\Theta/4$ | $3\Delta\Theta/4$ | $5\Delta\Theta/4$ | $7\Delta\Theta/4$ |
| $2\Delta\Theta$ | $5\Delta\Theta/4$ | $7\Delta\Theta/4$ | $9\Delta\Theta/4$ | $11\Delta\Theta/4$ |
| $3\Delta\Theta$ | $9\Delta\Theta/4$ | $11\Delta\Theta/4$ | $13\Delta\Theta/4$ | $15\Delta\Theta/4$ |
| $4\Delta\Theta$ | $13\Delta\Theta/4$ | $15\Delta\Theta/4$ | $17\Delta\Theta/4$ | $19\Delta\Theta/4$ |
| • | • | • | • | • |
| • | • | • | • | • |
| • | • | • | • | • |

As in the previous synthesis methods, the outputs of each beamformer are stored in memory and the stored outputs are subsequently pieced together in a linear combination in the manner described in Table IV to synthesize round-trip receive lines:

TABLE IV

Figure 23:
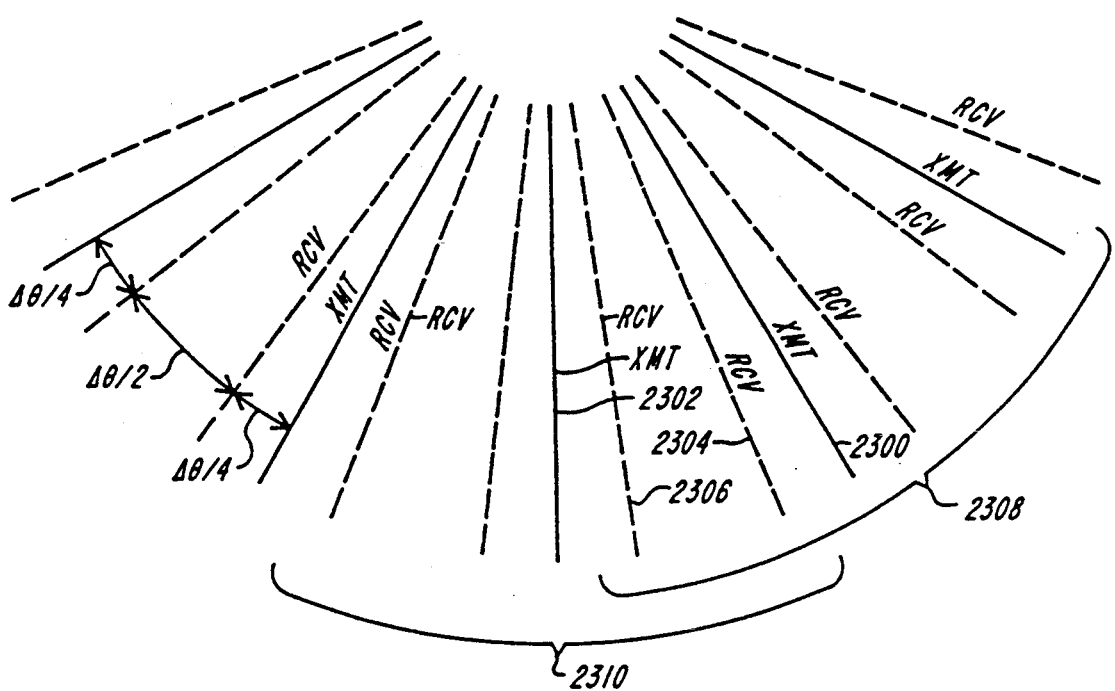
FIG. 23 is a schematic illustration of synthesized receive beam information in relation to transmit beam information using circuitry such as that shown in FIGS. 20 and 21 and received information from four parallel beams.

| Synthesized round-trip angle | Linear combination used to synthesize round-trip beam |
|---|---|
| • | • |
| • | • |
| $\Delta\Theta/4$ | $.93*R3(0) + .28*R1(\Delta\Theta)$ |
| $3\Delta\Theta/4$ | $.28*R4(0) + .93*R2(\Delta\Theta)$ |
| $5\Delta\Theta/4$ | $.93*R3(\Delta\Theta) + .28*R1(2\Delta\Theta)$ |
| $7\Delta\Theta/4$ | $.28*R4(\Delta\Theta) + .93*R2(2\Delta\Theta)$ |
| $9\Delta\Theta/4$ | $.93*R3(2\Delta\Theta) + .28*R1(3\Delta\Theta)$ |
| • | • |
| • | • | where Rn(x) is the stored output signal generated by beamformer n while from data received from a transmit beam shot at steering angle x. This combination results in the synthesized beams shown schematically in FIG. 23.

As before, the actual transmit beams are schematically illustrated as solid lines and the synthesized receive beams are shown as dotted lines. In the latter method, all receive beams are synthesized from two transmit beams. For example, receive beams 2304 and 2306 are synthesized from data received from transmit beams 2300 and 2302. Brackets 2308 and 2310 identify indicate groups of parallel receive beams synthesized from transmit data. As with the previous three beam method, there is a slight signal-to-noise ratio gain and some sensitivity to object motion. However, the four beam method has an advantage that all synthesized beams has virtually identical beam profiles for all round-trip angles and therefore there will not be a "checkerboard" artifact.

Although only a few embodiments of the inventive method and apparatus have been described, several modifications and changes will be immediately apparent to those skilled in the art. These modifications and other obvious changes are intended to be covered by the following claims.

What is claimed is:

1. Apparatus for increasing the image resolution of a phased array acoustic imaging system having a plurality of acoustic transducer elements, a transmitter coupled to said plurality of transducer elements for generating a transmit acoustic beam for interrogating an object, and a receiver coupled to said plurality of transducer elements for receiving signals from a receive acoustic beam, said apparatus comprising:
   a beamformer responsive to the received signals for generating image signals in a first format;
   a converter separate from said beamformer and responsive to said image signals for generating image display signals in a second format suitable for visual display;
   a circuit coupled to said converter for detecting and limiting said image display signals; and
   a display unit responsive to the detected and limited image display signals for visually displaying an image of said object.

2. Apparatus according to claim 1 wherein said converter converts image signals in an R-$\Theta$ format to image signals in an X-Y format.

3. Apparatus according to claim 1 wherein said circuit comprises a detector responsive to said image display signals for generating detected image signals and a limiting amplifier responsive to said detected image signals for generating signals suitable for visual display.

4. Apparatus according to claim 1 wherein said display unit comprises a video display monitor.

5. A method for increasing the image resolution of a phased array acoustic imaging system having a plurality of acoustic transducer elements, a transmitter coupled to said plurality of transducer elements for generating a transmit acoustic beam for interrogating an object, and a receiver coupled to said plurality of transducer elements for receiving signals from a receive acoustic beam, said method comprising the steps, in the order listed, of:
   A. generating image signals in a first format in response to the received signals and separately converting the image signals to image display signals in a second format suitable for visual display;
   B. detecting and limiting said image display signals; and
   C. visually displaying the image display signals detected and limited in step B as an image of said object.

6. A method according to claim 5 wherein step A comprises the step of:
   A1. converting image signals from an R-$\Theta$ format to an X-Y format.

7. A method according to claim 5 wherein step B comprises the steps of:
   B1. detecting said image display signals with a square-law detector; and
   B2. limiting said detected image signals by passing said detected image signals through a limiting amplifier.

8. A method according to claim 5 wherein step C comprises the step of:
   C1. displaying image display signals detected and limited in step B on a television monitor.

9. A phased-array acoustic imaging system for generating a visual image of an object comprising:
   a plurality of acoustic transducer elements;
   a transmitter coupled to said plurality of transducer elements for generating a transmit acoustic beam for interrogating said object;
   a receiver coupled to said plurality of transducer elements for receiving signals from a receive acoustic beam reflected from said object;
   a beamformer responsive to the received signals for generating image signals in a first format;
   a converter responsive to said image signals for generating image display signals in a second format suitable for visual display;
   a circuit coupled to said converter for detecting and limiting said image display signals; and
   a display unit responsive to the detected and limited image display signals for visually displaying an image of said object.

10. A phased-array acoustic imaging system according to claim 9 wherein said transmitter comprises means for generating a selectively delayed acoustic signal and means for applying the delayed acoustic signal to at least some of said plurality of transducer elements.

11. A phased-array acoustic imaging system according to claim 9 wherein said beamformer comprises means for selectively delaying the received signals and means for summing the selectively delayed received signals to generate said image signals in an R-$\Theta$ format.

12. A phased-array acoustic imaging system according to claim 11 wherein said converter comprises means responsive to said image signals in said R-$\Theta$ format for interpolating said signals to generate said image display signals in an X-Y format.

13. A phased-array acoustic imaging system according to claim 9 wherein said circuit comprises a diode detector responsive to said image display signals for generating detected image signals and a data compression device responsive to said detected image signals for generating signals suitable for visual display.

14. A phased-array acoustic imaging system according to claim 9 wherein said display unit comprises a video display monitor.

* * * * *